United States Patent [19]

Merger et al.

[11] Patent Number: 5,300,678
[45] Date of Patent: Apr. 5, 1994

[54] PREPARATION OF (107-SUBSTITUTED URETHANO ALKYLCARBOXYLATES)

[75] Inventors: Franz Merger, Frankenthal; Martin Brudermueller, Mannheim, both of Fed. Rep. of Germany

[73] Assignee: BASF Aktiengesellschaft, Ludwigshafen, Fed. Rep. of Germany

[21] Appl. No.: 14,168

[22] Filed: Feb. 5, 1993

[30] Foreign Application Priority Data

Feb. 7, 1992 [DE] Fed. Rep. of Germany ....... 4203457

[51] Int. Cl.$^5$ ............................................ C07C 261/00
[52] U.S. Cl. ..................... 560/157; 560/24; 560/32; 560/115; 560/162; 560/163
[58] Field of Search ................. 560/157, 24, 32, 115, 560/162, 163

[56] References Cited

U.S. PATENT DOCUMENTS 3,078,301 2/1963 Taub .

OTHER PUBLICATIONS

J. Org. Chem. 1983, 48, 2424–2426, Aust. J. Chem., 1976, 29, 2651–65, Central Nervous System Active Compounds . . .

Primary Examiner—Michael L. Shippen
Attorney, Agent, or Firm—Keil & Weinkauf

[57] ABSTRACT

A process for the preparation of a ω-(O-substituted urethano)alkylcarboxylate, wherein a lactam having from 4 to 9 ring members, which can have alkyl, alkenyl, cycloalkyl, or aralkyl groups containing up to 12 carbon atoms as substituents, is reacted with a carbonic diester of an alkanol, alkenol, cycloalkanol, or aralkanol containing up to 16 carbon atoms, at a temperature of from 25° to 300° C. in the presence of a catalytically effective amount of a base.

6 Claims, No Drawings

PREPARATION OF (ω-SUBSTITUTED URETHANO ALKYLCARBOXYLATES)

The invention relates to a process for the preparation of ω-(O-substituted urethano)alkylcarboxylates from lactams.

U.S. Pat. No. 3,078,301 discloses that alkyl ω-(O-alkylurethano)carboxylates are obtained by reacting a lactam with an alkali metal hydroxide to form the corresponding alkali metal lactam, and reacting an alkyl chlorocarbonate in a second stage with said alkali metal lactam. This process suffers from the drawback that it proceeds in two stages, and, moreover, substandard waste-waters containing chloride ions are formed.

In another process, described in J. Org. Chem. Vol. 48, pp. 2424 to 2426 (1983), δ-valerolactam is reacted with tert-butyl oxydiformate in a first stage to form N-tert-butoxycarbonylvalerolactam, which is then broken down in a second stage with 1.1 equivalents of sodium methylate to form methyl 5-(O-tert.-butylurethano)valerate.

Finally, Austr. J. of Chem. Vol. 29, pp. 2651 to 2665 (1976) discloses a process in which caprolactam is converted, in a first stage, to its sodium salt, and this sodium salt of the caprolactam is then reacted with diethyl carbonate, and ethyl 6-(O-ethylurethano)carboxylate is obtained. Emphasis is placed on the fact that the entire caprolactam must be converted to the sodium salt using sodium hydride before the second reaction takes place. Both of the aforementioned processes suffer from the drawback that they proceed in two stages, and solvents must be used for the preparation of the alkali metal lactams.

It is thus an object of the invention to provide a process for the preparation of ω-(O-substituted urethano)-carboxylates, in which the reaction is carried out in a single stage and gives good yields, non-chlorine-containing waste-waters are formed, and no additional solvents need be used.

This object is achieved in a process for the preparation of ω-(O-substituted urethano)alkylcarboxylates, wherein a lactam having from 4 to 9 ring members, which can have alkyl, alkenyl, cycloalkyl, or aralkyl groups containing up to 12 carbon atoms as substituents, is reacted with a carbonic diester of an alkanol, alkenol, cycloalkanol, or aralkanol containing up to 16 carbon atoms, at a temperature of from 25° to 300° C. in the presence of a catalytically effective amount of a base.

Our novel process has the advantage that it produces high yields in a single stage, no substandard chloride-containing waste-waters are formed, and no additional solvents need be used.

According to the present invention, the starting point comprises lactams having from 4 to 9 ring members, which can have alkyl, alkenyl, cycloalkyl oder aralkyl groups containing up to 12 carbon atoms as substituents. The lactams used advantageously have up to 2 substituents, preferably alkyl radicals having from 1 to 4 carbon atoms. Most particularly preferred substances are lactams having from 5 to 9 ring members with no further substituents. Suitable lactams are, for example, azetidinone, butyrolactam(2-pyrrolidinone), δ-valerolactam(2-piperidinone), ε-caprolactam, 7-aminoheptolactam, and ω-capryllactam.

The aforementioned lactams are reacted with carbonic diesters of alkenols, alkanols, cycloalkanols, or aralkanols having up to 16 carbon atoms, advantageously in excess. The alcohol moieties contained in the carbonic diesters may be the same or different. The alkanols, alkenols, cycloalkanols, or aralkanols may also have alkoxy radicals having from 1 to 4 carbon atoms. Carbonic diesters are preferred which are derived from alkanols or alkenols having from 1 to 6 carbon atoms, cyclohexanol, or benzyl alcohol. Special significance is attributable to carbonic diesters of alkanols or alkenols having from 1 to 3 carbon atoms. Suitable carbonic diesters are for example dimethyl carbonate, diethyl carbonate, dipropyl and diisopropyl carbonates, diallyl carbonate, dimethallyl carbonate, di-n-butyl carbonate, dicyclohexyl carbonate, or diisobutyl carbonate.

The reaction is carried out in the presence of catalytically effective amounts of a base. It is advantageous to use as bases hydroxides of alkali metals or alkaline-earth metals, alcoholates of alkali metals or alkaline-earth metals, e.g. of alcohols having from 1 to 6 carbon atoms. Special significance is attributable to sodium, potassium, lithium, and calcium alcoholates containing 1–4 carbon atoms. Sodium methylate or sodium ethylate and sodium or potassium tert-butylate are suitable, for example. Other suitable basic catalysts are amides of alkali metals or alkaline-earth metals, e.g., sodium amide or lithium amide. Highly suitable substances are amine bases, in particular tertiary amines, such as N-dimethylaniline, butyldimethylamine, and amidines such as 1,4-diazabicyclo[2.2.2]octane or 1,8-diazabicyclo[5.4.0]undecene-7. It is advantageous to use bases in a concentration of from 0.1 to 30 mol % and preferably from 0.1 to 10 mol %, based on lactam. The reaction is carried out at a temperature of from 25° to 300° C. It is advantageous to use a temperature of from 40° to 100° C.

It is advantageous to use, for each mole of lactam, from 1.0 to 5 mol of carbonic acid diester. Is has been found to be particularly advantageous to use from 1.05 to 4 and preferably from 1.2 to 2.5 mol of carbonic diester for each mole of lactam, which diester also serves as solvent.

Usually, the reaction is carried out under standard pressure conditions. If desired, it is possible to use a slightly reduced or slightly elevated pressure, e.g. a pressure of up to 2 bar. It is advantageous to keep the components in the liquid phase. The reaction can be carried out continuously or batchwise.

The catalyst is extracted from the reaction mixture obtained, usually with water, and the ω-(O-substituted urethano)-carboxylates are then isolated by distillation.

Alkyl ω-(O-substituted urethano)-carboxylates are valuable polymer building blocks, or are suitable for the preparation of ω-isocyanatocarboxylates.

The process of the invention may be illustrated with reference to the following examples.

EXAMPLES

EXAMPLE 1

In a stirred flask there are stirred 508 g of caprolactam (4.5 mol), 1,044 g of di-n-butyl carbonate (6 mol) and 12 g of sodium methylate (5 mol %) at 60° C. Following a reaction time of 2 h, the degree of conversion is >98%. After washing the organic phase with water and removing, by distillation, unconverted di-n-butyl carbonate, 1,227 g of butyl 6-(O-butylurethano)caproate are isolated (yield 95%, purity 96%).

EXAMPLE 2

113 g of caprolactam (1 mol), 94.5 g of dimethyl carbonate (1.05 mol) and 2.7 g of sodium methylate (5 mol %) are stirred at 130° C. After 0.5 h, the degree of conversion is 98%. After washing the organic phase with water and removing, by distillation, the unconverted dimethyl carbonate, 189 g of methyl 6-(O-methylurethano)caproate are isolated (yield 93%).

EXAMPLE 3

226 g of caprolactam (2 mol), 510 g of dimethallyl carbonate (3 mol) and 5.4 g of sodium methylate (0.5 mol %) are stirred at 60° C. After 1 h, the degree of conversion is >98%. After washing the organic phase with water, the product obtained comprises, following the removal, by distillation, of unconverted dimethallyl carbonate, 480 g of methallyl 6-(O-methallylurethano)-caproate (yield 85%, purity 97%).

EXAMPLE 4

113 g of caprolactam (1 mol), 180 g of dimethyl carbonate (2 mol), and 0.5 g of sodium methylate (1 mol %) are stirred at 60° C. Following a reaction time of 2 h, the degree of conversion is >97%. After washing the organic phase with water and the removal, by distillation, of unconverted dimethyl carbonate, 193 g of methyl 6-(O-methylurethano)-caproate are isolated (yield 95%, purity 96%).

EXAMPLE 5

113 g of caprolactam (1 mol), 180 g of dimethyl carbonate (2 mol), and 2 g of sodium methylate (5 mol %) are stirred at 60° C. Following a reaction time of 4 h, the degree of conversion is >95%. After washing the organic phase with water and the removal, by distillation, of unconverted dimethyl carbonate and caprolactam, 187 g of methyl 6-(O-methylurethano)-caproate are isolated (yield 92%, purity 96%).

EXAMPLE 6

113 g of caprolactam (1 mol), 180 g of dimethyl carbonate (2 mol), and 2 g of sodium amide (5 mol%) are stirred at 60° C. Following a reaction time of 10 h, the degree of conversion is >90%. After washing the organic phase with water and the removal, by distillation, of unconverted dimethyl carbonate, 173 g of methyl 6-(O-methylurethano)-caproate are isolated (yield 85%).

EXAMPLE 7

21 g of butyrolactam (2-pyrrolidinone) (0.25 mol), 29 g of dimethyl carbonate (0.32 mol), and 0.7 g of sodium methylate (5 mol %) are reacted at 80° C. After 8 h, the degree of conversion is ca 70%. After washing the organic phase with water and the removal, by distillation, of unconverted dimethyl carbonate and butyrolactam, methyl 4-(O-methylurethano)-butyrate is obtained at a selectivity of >95%.

EXAMPLE 8

25 g of valerolactam (2-piperidinone) (0.25 mol), 29 g of dimethyl carbonate (0.32 mol), and 0.7 g of sodium methylate (5 mol %) are reacted at 80° C. After 8 h, the degree of conversion is ca 80%. After washing the organic phase with water and the removal, by distillation, of unconverted dimethyl carbonate and valerolactam, methyl 5-(O-methylurethano)-valerate is obtained at a selectivity of >96%.

EXAMPLE 9

57 g of caprolactam (0.5 mol), 45 g of dimethyl carbonate (0.5 mol), and 10 g of N,N-dimethylaniline (16 mol %) are reacted at 250° C. in an autoclave. Following a reaction time of 10 h, the degree of conversion is 72%. After washing the organic phase with water and distillation, 31 g of methyl 6-(O-methylurethano)-caproate are obtained (yield 35%).

We claim:

1. A one-step process for the preparation of a ω-(O-substituted urethano)alkylcarboxylate, wherein a lactam having from 4 to 9 ring members, which can have alkyl, alkenyl, cycloalkyl, or aralkyl groups containing up to 12 carbon atoms as substituents, is reacted with a carbonic diester of an alkanol, alkenol, cycloalkanol, or aralkanol containing up to 16 carbon atoms, at a temperature of from 25° to 300° C. in the presence of from 0.1 to 30 mole %, based on lactam, of a base.

2. A process as claimed in claim 1, wherein a temperature of from 40° to 100° C. is maintained.

3. A process as claimed in claim 1, wherein the base used is an alkali metal alcoholate of an alkanol having from 1 to 4 carbon atoms, an alkali metal or alkaline-earth metal amide, or an amine.

4. A process as claimed in claim 1, wherein from 1 to 5 mol of carbonic diester are employed for each mole of lactam.

5. A process as claimed in claim 1, wherein a lactam having from 5 to 9 ring members is used.

6. A process as claimed in claim 1, wherein a carbonic diester of an alkanol or alkenol having from 1 to 4 carbon atoms is used.

* * * * *

UNITED STATES PATENT AND TRADEMARK OFFICE
CERTIFICATE OF CORRECTION

PATENT NO.: 5,300,678

DATED: April 5, 1994

INVENTOR(S): MERGER et al.

It is certified that error appears in the above-identified patent and that said Letters Patent is hereby corrected as shown below:

On the title page, item [54], delete "107" and insert -- $w$ --;

delete the ")" after "ALKYLCARBOXYLATES" and insert it after "URETHANO".

Signed and Sealed this

Twentieth Day of September, 1994

Attest:

BRUCE LEHMAN

Attesting Officer  Commissioner of Patents and Trademarks